United States Patent
Simpson et al.

(10) Patent No.: US 7,273,485 B2
(45) Date of Patent: Sep. 25, 2007

(54) BALLOON CATHETER HAVING A SHAFT WITH A VARIABLE STIFFNESS INNER TUBULAR MEMBER

(75) Inventors: John A. Simpson, Carlsbad, CA (US); Jessie Delgado, Murrieta, CA (US); Bruce Wilson, Temecula, CA (US); Lenny Barbod, San Diego, CA (US); Ramon Torres, Temecula, CA (US); Devon Brown, Temecula, CA (US); Quan Ritchie, Moreno Valley, CA (US); William S. Chin, Moreno Valley, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 676 days.

(21) Appl. No.: 10/392,697

(22) Filed: Mar. 20, 2003

(65) Prior Publication Data

US 2004/0186506 A1   Sep. 23, 2004

(51) Int. Cl.
*A61M 25/10* (2006.01)
*A61M 29/02* (2006.01)

(52) U.S. Cl. .................................. 606/194
(58) Field of Classification Search ............ 604/96.01–103.14; 600/585; 606/192–194
See application file for complete search history.

(56) References Cited

U.S. PATENT DOCUMENTS

| | | | |
|---|---|---|---|
| 4,877,031 A * | 10/1989 | Conway et al. ............ 606/194 |
| 4,892,519 A * | 1/1990 | Songer et al. ......... 604/102.03 |
| 5,156,594 A | 10/1992 | Keith |
| 5,496,275 A * | 3/1996 | Sirhan et al. ............ 604/96.01 |
| 5,743,875 A | 4/1998 | Sirhan et al. |
| 5,911,715 A * | 6/1999 | Berg et al. .................. 604/525 |
| 6,179,856 B1 | 1/2001 | Barbere |
| 6,306,124 B1 * | 10/2001 | Jones et al. ................. 604/509 |
| 6,585,687 B1 * | 7/2003 | Shkolnik ................. 604/96.01 |
| 6,589,226 B1 | 7/2003 | Owens |
| 6,893,456 B2 | 5/2005 | Lumauig |

OTHER PUBLICATIONS

Cordis' product brochure; The Journey Inspires the Design, AQUA T3.

* cited by examiner

*Primary Examiner*—Anhtuan T. Nguyen
*Assistant Examiner*—Elizabeth Houston
(74) *Attorney, Agent, or Firm*—Fulwider Patton LLP

(57) ABSTRACT

A catheter having an elongated shaft and a balloon on a distal shaft section, the elongated shaft comprising an outer tubular member, and an inner tubular member which has a bonded portion along which an outer surface of the inner tubular member is bonded to an inner surface of the outer tubular member. The inner tubular member has a proximal portion proximal to the bonded portion, and a distal portion distal to the bonded portion with higher axial compression stiffness and column strength than the proximal portion thereof. The catheter has improved traceability, axial collapse resistance, pushability, and crossability, for improved ability to position the balloon at a desired location in a patient's body lumen.

21 Claims, 3 Drawing Sheets

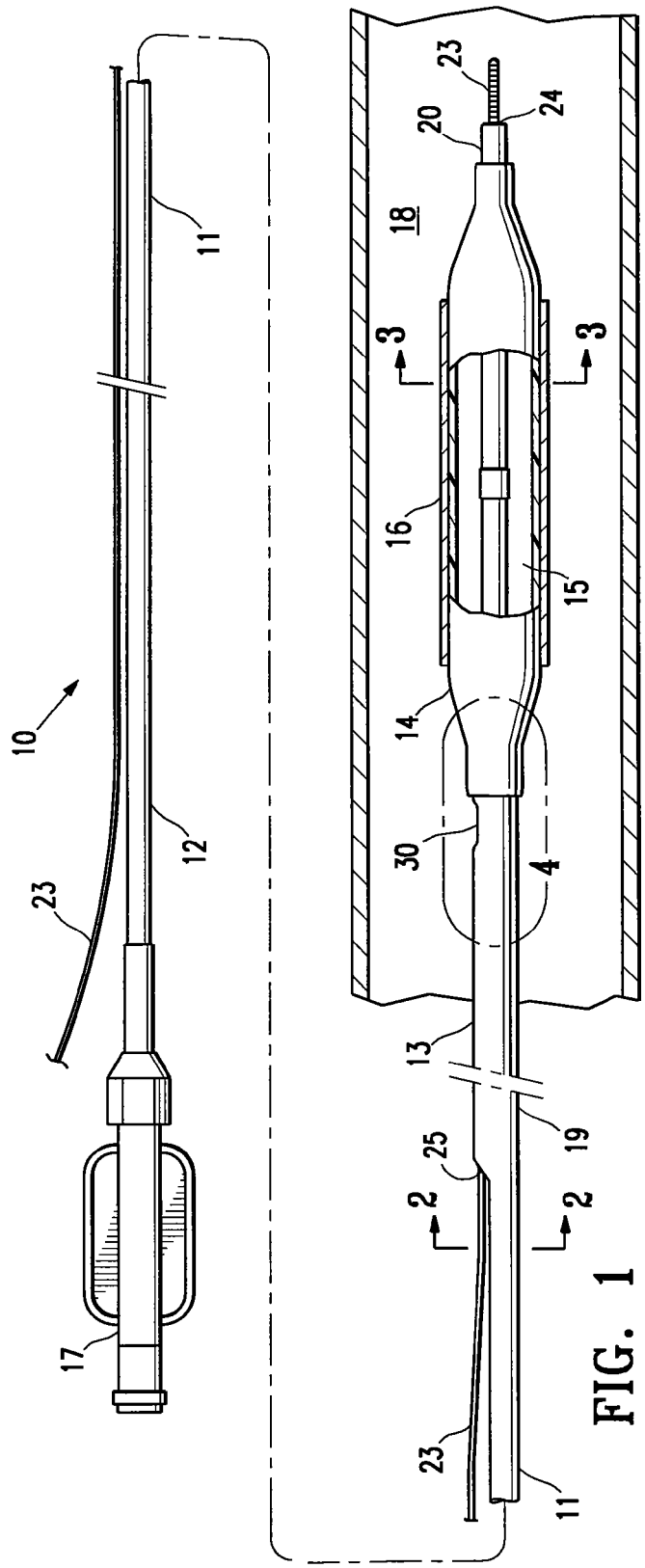
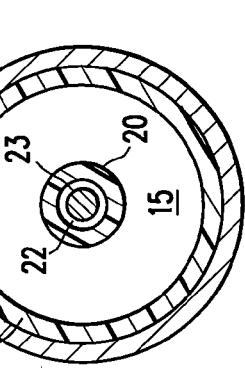
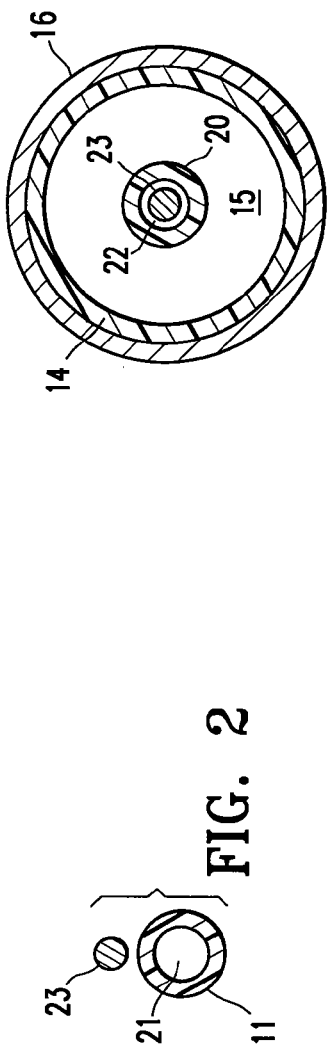
FIG. 1
FIG. 2
FIG. 3

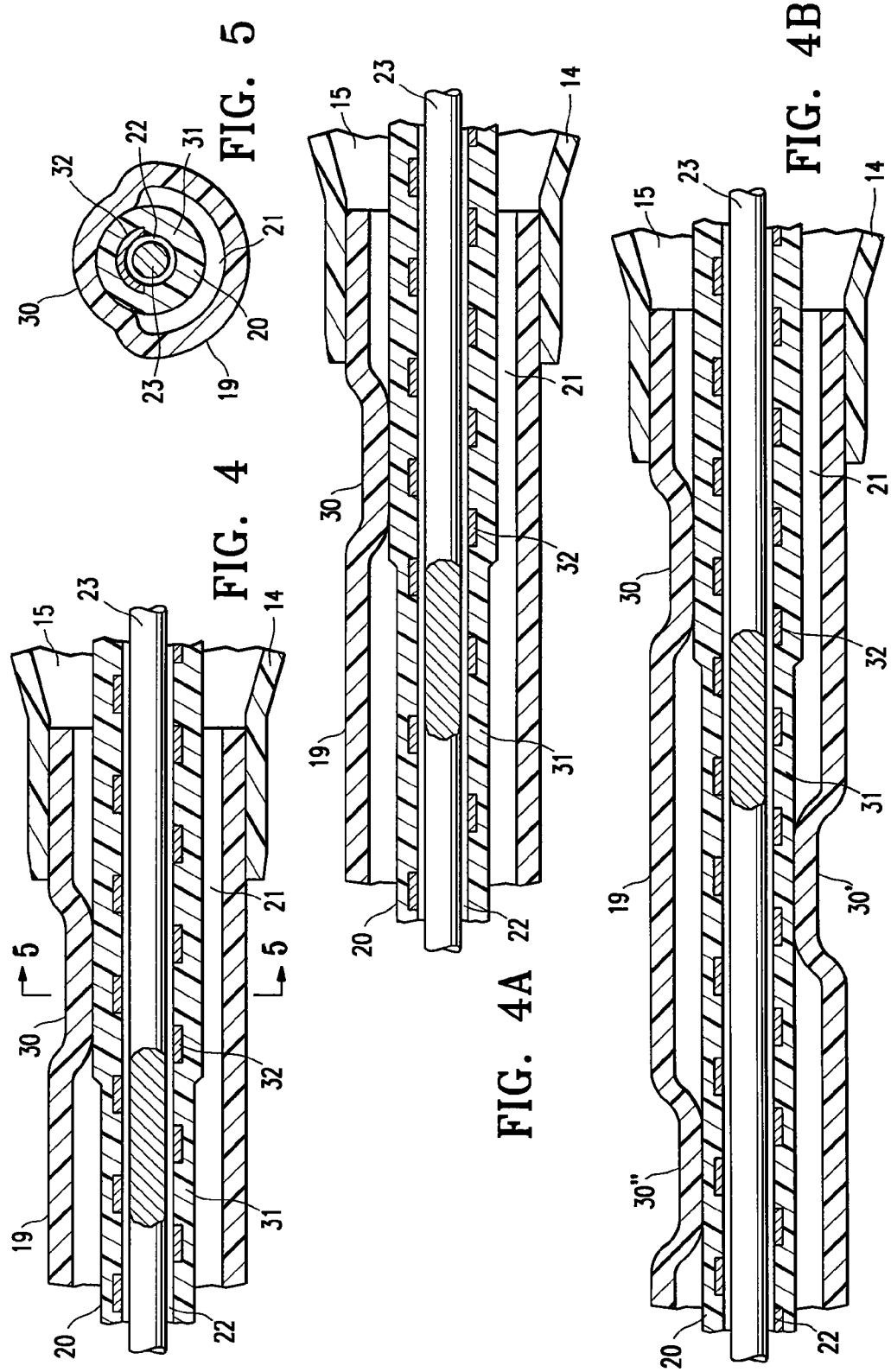

BALLOON CATHETER HAVING A SHAFT WITH A VARIABLE STIFFNESS INNER TUBULAR MEMBER

BACKGROUND OF THE INVENTION

This invention generally relates to catheters, and particularly intravascular catheters for use in percutaneous transluminal coronary angioplasty (PTCA) or for the delivery of stents.

In percutaneous transluminal coronary angioplasty (PTCA) procedures a guiding catheter is advanced in the patient's vasculature until the distal tip of the guiding catheter is seated in the ostium of a desired coronary artery. A guidewire is first advanced out of the distal end of the guiding catheter into the patient's coronary artery until the distal end of the guidewire crosses a lesion to be dilated. A dilatation catheter, having an inflatable balloon on the distal portion thereof, is advanced into the patient's coronary anatomy over the previously introduced guidewire until the balloon of the dilatation catheter is properly positioned across the lesion. Once properly positioned, the dilatation balloon is inflated with inflation fluid one or more times to a predetermined size at relatively high pressures so that the stenosis is compressed against the arterial wall and the wall expanded to open up the vascular passageway. Generally, the inflated diameter of the balloon is approximately the same diameter as the native diameter of the body lumen being dilated so as to complete the dilatation but not over expand the artery wall. After the balloon is finally deflated, blood resumes through the dilated artery and the dilatation catheter and the guidewire can be removed therefrom.

In such angioplasty procedures, there may be restenosis of the artery, i.e., reformation of the arterial blockage, which necessitates either another angioplasty procedure, or some other method of repairing or strengthening the dilated area. To reduce the restenosis rate of angioplasty alone and to strengthen the dilated area, physicians now normally implant an intravascular prosthesis, generally called a stent, inside the artery at the site of the lesion. Stents may also be used to repair vessels having an intimal flap or dissection or to generally strengthen a weakened section of a vessel or to maintain its patency. Stents are usually delivered to a desired location within a coronary artery in a contracted condition on a balloon of a catheter which is similar in many respects to a balloon angioplasty catheter, and expanded within the patient's artery to a larger diameter by expansion of the balloon. The balloon is deflated to remove the catheter and the stent left in place within the artery at the site of the dilated lesion. For details of stents, see for example, U.S. Pat. No. 5,507,768 (Lau, et al.) and U.S. Pat. No. 5,458,615 (Klemm, et al.), which are incorporated herein by reference.

An essential step in effectively performing a PTCA procedure is properly positioning the balloon catheter at a desired location within the coronary artery. To properly position the balloon at the stenosed region, the catheter must have good pushability (i.e., ability to transmit force along the length of the catheter), and good trackability and flexibility, to be readily advanceable within the tortuous anatomy of the patient's vasculature. Conventional balloon catheters for intravascular procedures, such as angioplasty and stent delivery, frequently have a relatively stiff proximal shaft section to facilitate advancement of the catheter within the patient's body lumen and a relatively flexible distal shaft section to facilitate passage through tortuous anatomy such as distal coronary and neurological arteries without damage to the vessel wall. However, one difficulty has been providing a catheter shaft having low bending stiffness for optimum trackability, while having sufficiently high axial stiffness (compression modulus) and column strength (collapse point) for maximum transmission of force to the catheter distal end. A shaft inner tubular member (extending through the balloon interior) having inadequate column stiffness may telescopically collapse under axial load causing balloon bunching/buckling during advancement of the catheter, which consequently inhibits positioning the balloon across a stenosis. Accordingly, it would be a significant advance to provide a catheter having an improved combination of flexibility, collapse resistance, pushability, and crossability.

SUMMARY OF THE INVENTION

The invention is directed to a balloon catheter having an elongated shaft and a balloon on a distal shaft section, the elongated shaft comprising an outer tubular member, and an inner tubular member with a bonded portion along which an outer surface of the inner tubular member is bonded to an inner surface of the outer tubular member. The inner tubular member has a distal portion distal to the bonded portion with higher axial compression stiffness and column strength than a proximal portion of the inner tubular member. The catheter has improved trackability, axial collapse resistance, pushability, and crossability, for improved ability to position the balloon at a desired location in a patient's body lumen.

A balloon catheter of the invention generally comprises an elongated shaft having a proximal shaft section, a distal shaft section, an inflation lumen, and a guidewire lumen, with a balloon on a distal shaft section. The elongated shaft is formed at least in part by an outer tubular member defining at least a section of the inflation lumen in fluid communication with an interior of the balloon, and by an inner tubular member defining at least a section of the guidewire lumen. The inner tubular member extends in at least a distal section of the outer tubular member and in the interior of the balloon, and in accordance with the invention has a bonded portion bonded to the outer tubular member. The guidewire lumen is in fluid communication with a proximal guidewire port, and a distal guidewire port at the distal end of the shaft. In one embodiment, the catheter is a rapid exchange type catheter having the proximal end of the inner tubular member in the distal shaft section located distal to the proximal end of the shaft, so that the guidewire proximal port is in the distal shaft section spaced a relatively short distance proximally from the guidewire distal port and a relatively long distance distally from the proximal end of the catheter shaft. In an alternative embodiment, the catheter is an over-the-wire type catheter having the inner tubular member proximal end located at a proximal end portion of the shaft so that the inner tubular member extends along the proximal and distal shaft sections.

The bonded portion of the inner tubular member links the inner tubular member to the outer tubular member, preferably at or adjacent to a stiffness transition in the inner tubular member. Specifically, a distal portion of the inner tubular member located distal to the bonded portion has a higher axial compression stiffness and column strength than a proximal portion of the inner tubular member located proximal to the bonded portion. Additionally, in one embodiment, the proximal portion of the inner tubular member has a lower bending stiffness than the distal portion of the inner tubular member. Preferably, the bonded portion is located at (i.e., radially aligned with) or longitudinally adjacent to the proximal end of the balloon. In a presently preferred embodiment, the bonded portion has a distal end located proximal to the balloon and typically a relatively short distance from the proximal end of the balloon and a relatively long distance from the proximal end of the inner tubular member. As a result, the length of the distal portion of the inner tubular member extending distally from the bonded portion, through the balloon interior to the distal end of the inner tubular member, is minimized relative to the length of the proximal portion of the inner tubular member. The configuration provides a maximum length to the highly flexible proximal portion of the inner tubular member. In one embodiment, the distal portion of the inner tubular member has a length equal to about 1 to about 5% of the length of the entire shaft. By linking a portion of the inner tubular member to the outer tubular member near the proximal end of the balloon, the axial compression stiffness of the proximal portion of the inner tubular member has little or no influence on the amount of axial load that is carried by the balloon. Consequently, in the catheter of the invention, the inner tubular member proximal portion has a low bending stiffness and a concurrently low axial stiffness, with the outer tubular member carrying a substantial portion of the total axial force along the shaft up to the adjoining balloon. Distal to the outer tubular member, the distal portion of the inner tubular member is provided with sufficient column stiffness and strength to prevent or inhibit it from elastically shortening or telescopically collapsing under axial load. As a result, the catheter shaft is highly flexible, and nonetheless transfers the majority of applied axial load to the distal end of the balloon and thereby prevents or inhibits buckling of the balloon during advancement of the catheter in the patient's body lumen.

The inner tubular member proximal portion typically is constructed so as to minimize its bending stiffness, thereby being less stiff in both bending stiffness and axial compression stiffness than the outer tubular member. The outer tubular member is provided with sufficient axial compression stiffness to carry a majority of the axial load without buckling. For example, in one embodiment, the proximal inner member carries only about 5 to about 25% of the total axial force transmitted to the distal end of the catheter. In one embodiment, the catheter is preferably an over-the-wire type catheter, due to the large reduction in the axial load carried by the balloon provided by the catheter configuration of the invention. In one embodiment, the axial load carried by the balloon in an over-the-wire catheter of the invention is lowered by about 40 to about 90%, compared to a conventional catheter without the inner tubular member bonded portion. In one embodiment, the axial load carried by the balloon in a rapid exchange catheter of the invention is lowered by about 40 to about 80%, compared to a conventional catheter without the inner tubular member bonded portion.

A variety of suitable methods may be used to form the inner tubular member stiffness transition between the proximal and distal portions thereof, to provide an inner member with a relatively low bending stiffness over the majority of its length but having greater axial stiffness (also known as compression modulus) and column strength (i.e., collapse point under axial load) distal to the bonded portion. In a presently preferred embodiment, at least part of the inner tubular member proximal portion has a first wall thickness, and at least part of the inner tubular member distal portion has a second wall thickness greater than the first wall thickness. Preferably, the part of the inner tubular member having the first wall thickness has an outer diameter smaller than an outer diameter of the part of the inner tubular member having the second (i.e., smaller) wall thickness, which thus increases the size of the inflation lumen defined by the space between the proximal portion of the inner tubular member and the inner surface of the outer tubular member. The variable wall thickness can be formed using a variety of processing methods during manufacture of the inner tubular member, including decreasing (as for example by necking) the wall thickness of the proximal portion and/or increasing the wall thickness of the distal portion. In an alternative embodiment, the distal portion of the inner tubular member is provided with the higher axial stiffness. For example, the axial stiffness of the distal portion can be increased by providing a reinforcing member (such as braiding, or a mandrel, or a flexible tubular splint member on an outer surface thereof), or by adding fiber reinforcement to the shaft jacketing, or by irradiating or heat stabilizing the polymeric material of the distal portion to increase its stiffness. In another embodiment, the inner tubular member distal portion is formed of a polymeric material having a higher Shore durometer hardness than the polymeric material of the proximal portion of the inner tubular member. The inner tubular member typically comprises a multilayered tubular member, so that the embodiment with a higher durometer polymeric material in the distal portion should be understood to refer to the durometer of at least one of the layers of the inner tubular member. The higher durometer material forming the distal portion may be the same type of polymeric material as the polymeric material of the proximal portion (i.e., a polyamide), or alternatively, a different type of polymeric material.

The bonded portion extends around part of the circumference of the inner tubular member, so that a nonbonded portion of the inner tubular member is radially adjacent to the bonded portion to provide a path for the inflation fluid past the bonded portion. The bonded portion generally extends around about 10% to about 90% of the circumference of the inner tubular member, and most preferably the percentage is minimized in order to maximize the fluid flow path past the bond. The length of the bonded portion is generally substantially less than the length of the inner tubular member, although in one embodiment, the inner tubular member includes one or more portions proximally spaced apart from the bonded portion, along which the outer surface of the inner tubular member proximal portion is bonded to the inner surface of the outer tubular member.

In a presently preferred embodiment, the inner tubular member comprises a polymeric tube with a coiled reinforcing member embedded therein. Although the distal portion of the inner tubular member typically has a higher axial compression stiffness and column strength than the proximal portion thereof, the coiled reinforcing member allows the inner tubular member to have a relatively low bending stiffness and high radial collapse resistance throughout, for excellent catheter trackability and guidewire movement even after inflation of the balloon at relatively high inflation pressures. The coiled reinforcing member preferably extends at least in part within the proximal and distal portions of the inner tubular member, and in one embodiment, the coiled reinforcing member extends along the entire length of the inner tubular member. In one embodiment, the coiled reinforcing member has a uniform pitch, stiffness, and/or column strength throughout its length. Alternatively, the coiled reinforcing member extending along the distal portion of the inner tubular member has a tighter coil pitch (i.e., more closely spaced coils) than along the proximal portion of the inner tubular member, or otherwise provided with a higher axial stiffness and column strength along the distal portion, to produce the stiffer distal portion of the inner tubular member. For example, a longitudinally extending wire member bonded to the distal portion of the coiled reinforcing member selectively stiffens the distal portion of the inner tubular member. In one embodiment, two types or plies of wire or ribbon form the reinforcing member, with the first type reinforcing the entire length of the inner tubular member and the second type located in the distal portion of the inner tubular member to selectively stiffen the distal portion of the inner tubular member by, for example, preventing the distal coils from moving closer together or bunching under axial load. Similarly, a braided reinforcing member having a variable pick count (number of braid crossover points per unit of axial length) imparting a stiffness transition may alternatively be used to form the inner tubular member. The resulting catheter shaft, formed by the inner and outer tubular members, has an improved low bending stiffness throughout the length of the inner member, for improved trackability.

In a method of making a balloon catheter embodying features of the invention, an elongated shaft having a proximal end, a distal end, an inflation lumen, and a guidewire lumen is assembled by placing an inner tubular member within at least a distal section of an outer tubular member, so that the inner tubular member defines the guidewire lumen and the outer tubular member defines the inflation lumen, the inner tubular member having a proximal portion with an axial compression stiffness and bending stiffness less than an axial compression stiffness and bending stiffness of a distal portion of the inner tubular member. A portion of the inner tubular member is then bonded to the outer tubular member at or adjacent a junction between the proximal and distal portions of the inner tubular member, to form a bonded portion along which an outer surface of the inner tubular member is bonded to an inner surface of the outer tubular member. A balloon is bonded to the distal shaft section so that the balloon has an interior in fluid communication with the inflation lumen, to form the balloon catheter.

The inner tubular member having a stiffness transition can be formed using a variety of suitable methods. For example, in one embodiment, forming the inner tubular member comprises necking a proximal part of a polymeric tube to reduce a wall thickness and an outer diameter thereof without reducing an inner diameter thereof, to thereby reduce the axial compression stiffness of the proximal part of the polymeric tube, and embedding a coiled reinforcing member in the polymeric tube. In another embodiment, forming the inner tubular member comprises increasing the wall thickness of a distal section of a polymeric tubular member having a coiled reinforcing member embedded therein, by a method selected from the group consisting of heat shrinking an outer polymeric layer onto the distal section of the coil reinforced polymeric tubular member, melt bonding an outer polymeric layer onto the distal section of the coil reinforced polymeric tubular member, or dip coating the distal section of the coiled reinforced polymeric tubular member. In another embodiment, forming the inner tubular member comprises joining the distal end of a first tube to a proximal end of a second tube to form a polymeric tubular member, and fusing the polymeric tubular member to a coiled reinforcing member, and the second tube is formed of a polymeric material having a higher Shore durometer hardness or has a wall thickness greater than a wall thickness of the first tube. In another embodiment, forming the inner tubular member comprises fusing a polymeric tube to a braided reinforcing member, the braided reinforcing member having a distal part with a pick count which is higher than a pick count of a proximal part of the braided reinforcing member. In another embodiment, forming the inner tubular member comprises applying an adhesive or melt bondable polymer to a portion of a mandrel, and applying a coil on the mandrel with a distal part of the coil on the adhesive or melt bondable polymer, and fusing a polymeric layer on the coil, to form the coil reinforced polymeric tubular member. In another embodiment, forming the inner tubular member comprises joining the distal end of a coil reinforced polymeric tubular member to the proximal end of a polymer tube having a greater axial stiffness and column strength than the coil reinforced polymeric tubular member. In another embodiment, forming the inner tubular member comprises irradiating or heat stabilizing a distal part of a polymeric tube to increase the stiffness of the distal part of the polymeric tube.

The balloon catheter of the invention has improved pushability and trackability, due to the low bending stiffness inner tubular member having a bonded portion bonded to the outer tubular member and excellent force transmission through the balloon interior to the distal tip. The shaft configuration prevents or inhibits the balloon from buckling or bunching during advancement in the patient's blood vessel, despite the low bending stiffness of the inner tubular member and resulting excellent trackability. Thus, the catheter shaft of the invention accommodates typically competing considerations in the design of catheters, to facilitate positioning the balloon at a desired location in the patient's blood vessel. These and other advantages of the invention will become more apparent from the following detailed description of the invention and the accompanying exemplary drawings.

BRIEF DESCRIPTION OF THE DRAWINGS

FIG. 1 is an elevational view, partially in section, of a rapid exchange type balloon catheter which embodies features of the invention.

FIGS. 2-3 are transverse cross sections of the catheter shown in FIG. 1, taken along lines 2-2 and 3-3, respectively.

FIG. 4 is an enlarged, longitudinal cross sectional view of the catheter shown in FIG. 1, taken within circle 4, and FIG. 4A illustrates an alternative embodiment in which the coiled reinforcing member extending along the distal portion of the inner tubular member has a tighter coil pitch than along the proximal portion of the inner tubular member, and FIG. 4B illustrates an alternative embodiment having intermittently bonded proximal bonded portions.

FIG. 5 is a transverse cross section of the catheter shown in FIG. 4, taken along line 5-5.

DETAILED DESCRIPTION OF THE PREFERRED EMBODIMENTS

Figure 6:
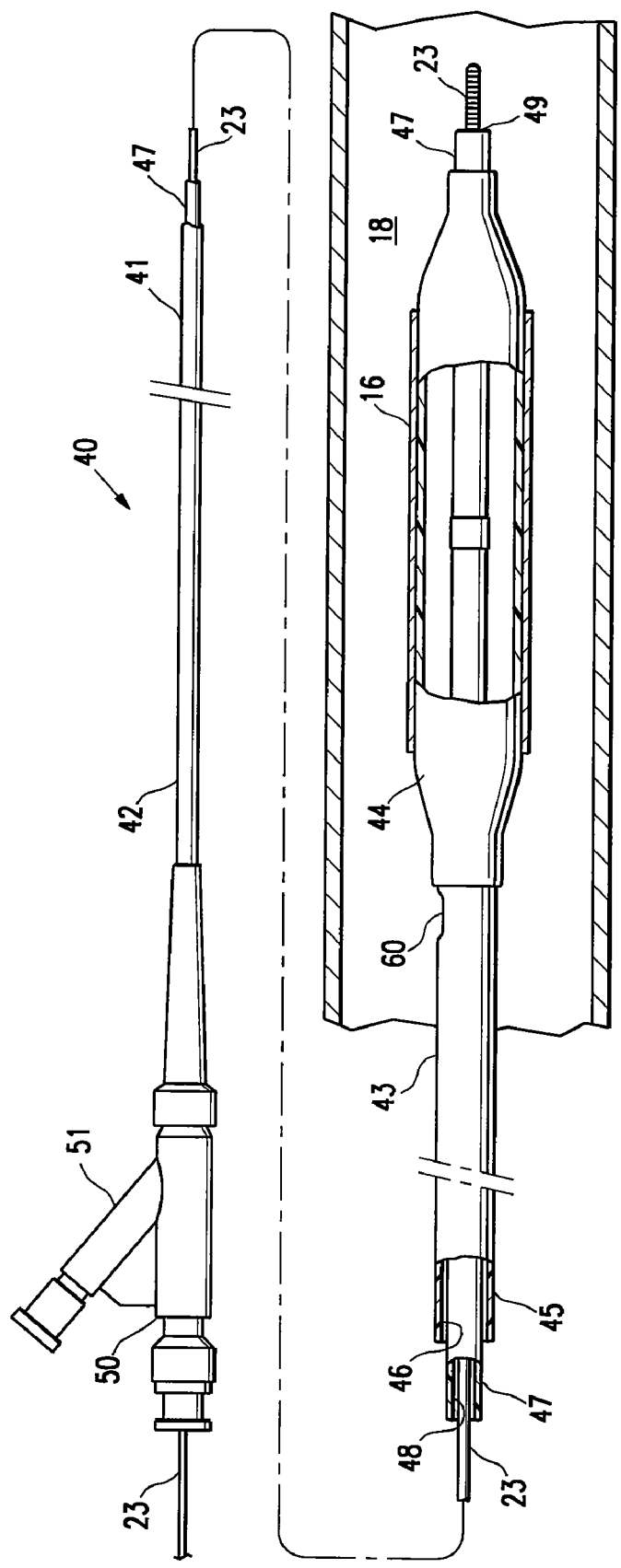
FIG. 6 is an elevational view, partially in section, of an over-the-wire type balloon catheter which embodies features of the invention

FIG. 1 illustrates rapid exchange type balloon catheter 10 embodying features of the invention. Catheter 10 generally comprises an elongated catheter shaft 11 having a proximal end, a distal end, a proximal shaft section 12 and a distal shaft section 13 at the distal end of the proximal shaft section, and an inflatable balloon 14 on the distal shaft section. The shaft 11 has an inflation lumen 21, and a guidewire receiving lumen 22. The proximal shaft section 12 comprises a proximal tubular member defining a proximal portion of the inflation lumen 21. The distal shaft section 13 comprises an outer tubular member 19 defining a distal portion of the inflation lumen 21, and an inner tubular member 20 defining the guidewire lumen 22 in fluid communication with a guidewire distal port 24 at the distal end of the catheter and a guidewire proximal port 25 at the proximal end of the inner tubular member 20, configured to slidably receive guidewire 23 therein. Balloon 14 has a proximal end sealingly secured to the distal end of outer tubular member 19 and a distal end sealingly secured to the distal end of inner tubular member 20, so that its interior is in fluid communication with inflation lumen 21. An adapter 17 at the proximal end of the catheter provides access to the inflation lumen 21. FIG. 1 illustrates the balloon 14 in a low profile configuration, prior to inflation, for introduction and advancement within the patient's body lumen 18, with a stent 16 mounted on the working length of the balloon 14. In use, the distal end of catheter 10 is advanced to a desired region of the patient's body lumen 18 in a conventional manner either over previously positioned guidewire 23, or with guidewire 23 already in the catheter 10. The balloon 14 is inflated to expand the stent 16, and the balloon deflated, and the catheter 10 removed from or repositioned within the body lumen 18, leaving stent 16 implanted in the body lumen 18. Although illustrated as a stent delivery catheter in the embodiment of FIG. 1, the balloon catheter 10 of the invention may be configured to perform a variety of medical procedures including dilating a stenosis. Similarly, rapid exchange type catheter 10 of the embodiment of FIG. 1 may comprise a variety of suitable rapid exchange catheter shaft configurations as are conventionally known. FIGS. 2 and 3 illustrate transverse cross sectional views of the catheter of FIG. 1, taken along lines 2-2 and 3-3, respectively.

The inner tubular member 20 has a bonded portion 30 along which the outer surface of the inner tubular member is bonded to the inner surface of the outer tubular member 19, as best shown in FIG. 4, illustrating an enlarged longitudinal cross section of the, catheter of FIG. 1, taken within circle 4. The bonded portion is proximally adjacent to the proximal end of the balloon 14, with a distal end proximal to the balloon 14. The bonded portion 30 is typically spaced proximally apart from the proximal end of the balloon a sufficient distance, so that forming the bonding portion 30 does not damage the balloon 14 secured to the outer tubular member 19. For example, in one embodiment, the distal end of the bonded portion is within about 0.5 to 2 cm from the proximal end of the balloon. However, the bonded portion 30 can have a variety of suitable locations. For example, the bonded portion 30 can alternatively extend at least in part underneath the balloon proximal skirt section (i.e., radially aligned therewith), with the distal end of the bonded portion located distal to the proximal end of the balloon, provided the balloon 14 is not damaged by the bonding process.

Preferably, the bonded portion 30 length is about 0.1 to about 2 cm, which in the rapid exchange catheter of FIG. 1 is about 0.4% to about 8% of the length of the inner tubular member 20 (the inner tubular member 20 having a length of about 20 to about 30 cm). The bonded portion 30 extends partially around the circumference of inner tubular member 20, as best shown in FIG. 5 illustrating a transverse cross section of FIG. 4, taken along line 5-5. In the illustrated embodiment, the bonded portion extends around about 30% to about 40% of the inner tubular member circumference.

In one embodiment, the bonded portion 30 is formed by heating and applying a radially inward force to press a portion of the outer tubular member 19 down onto the underlying inner tubular member 20 using a crescent shaped mandrel to preserve the inflation lumen. As a result, the outer diameter of the distal shaft 13 is decreased along the bonded portion 30. The inflation lumen 21 and guidewire lumen 22 are in a side-by-side relation along the length of the bonded portion 30. In the embodiment of FIG. 1, proximal to the bonded portion 30, the outer and inner tubular members 19, 20 are separate although they may be intermittently bonded in like manner at other more proximal locations. A continuous bond line is not recommended however because of the accompanying increase in bending stiffness. The bond between the outer and inner tubular members 19, 20 along the bonded portion 30 is preferably a fusion bond, although the bond may alternatively or additionally be an adhesive bond. For example, the outer and inner tubular members 19, 20 are heated along the length of the desired bonded portion, typically with a mandrels in the lumens 21, 22 and heat shrink tubing (not shown) positioned around the outer tubular member 19, to soften and melt bond the tubular members together. The tubular members 19, 20 are preferably heated using a laser and the heat directed only along the part of the circumference of the outer tubular member to be bonded to the inner tubular member to reduce heat spread during formation of bonded portion 30. However, a variety of suitable heating methods may be used including using a hot air heating nozzle and heating the entire circumference of the outer tubular member.

In the embodiment illustrated in FIG. 4, the bonded portion 30 is formed by directly bonding the outer and inner tubular members 19, 20 together. However, in an alternative embodiment, a tube (not shown) may be provided in the inflation lumen 21 which has an outer surface bonded to both the outer surface of the inner tubular member and to the inner surface of the outer tubular member, to thereby bond the outer and inner tubular members together to form bonded portion 30 (i.e., the tube is only on one side of the inner tubular member), and the inner tubular member may therefore be coaxial with the outer tubular member.

The inner tubular member 20 has a proximal portion proximal to the bonded portion 30, and a distal portion distal to the bonded portion 30. The distal portion of the inner tubular member 20 has a higher axial compressive stiffness and column strength than the proximal portion of the inner tubular member 20. In the embodiment of FIG. 4, the distal portion of the inner tubular member 20 has a larger wall thickness and a larger outer diameter than the proximal portion of the inner tubular member 20, although a variety of suitable methods may be used to provide the inner tubular member stiffness transition. The reduced outer diameter of the proximal portion of the inner tubular member 20 increases the size of the inflation lumen 21 extending therealong, for more rapid inflation/deflation. Additionally, the smaller wall thickness of the proximal portion of the inner tubular member 20 provides the proximal portion of the inner tubular member 20 with a lower bending stiffness than the distal portion thereof.

In the embodiment of FIG. 4, the wall thickness of the inner tubular member 20 along the bonded portion 30 is greater than the wall thickness of the inner tubular member proximal portion. Specifically, the proximal end of the bonded portion 30 is radially aligned with the proximal end of the part of the inner tubular member having the larger wall thickness than the proximal portion of the inner tubular member. The stiffness transition provided by the change in wall thickness of the inner member preferably takes place over a relatively short length, to provide maximum benefit of the lower bending stiffness of the proximal inner member. In the embodiment of FIG. 4, the outer diameter of the inner tubular member tapers proximally to the smaller outer diameter of the proximal portion along a length of about 1 mm.

The inner tubular member preferably comprises a polymeric tube 31 with a coiled reinforcing member 32 embedded therein. In the embodiment of FIG. 4, the coiled reinforcing member 32 is a coiled flat ribbon, spiraling along the length of the inner tubular member with uniformly spaced-apart coils. However, a variety of suitable reinforcing members may be used as are conventionally known, including a coiled round wire. FIG. 4A illustrates an alternative embodiment in which the coiled reinforcing member 32 extending along the distal portion of the inner tubular member has a tighter coil pitch (i.e., more closely spaced coils) than along the proximal portion of the inner tubular member. The coiled reinforcing member extends at least in part within the proximal and distal portions of the inner tubular member 20, and preferably extends along substantially the entire length of the inner tubular member 20 to prevent radial collapse under extreme balloon inflation pressures. Although the polymeric tube 31 is shown as a single layered member for ease of illustration, it should be understood that the polymeric tube 31 is typically a multilayered polymeric member, as for example with an inner lubricious polymeric layer, and an outer polymeric layer coextruded or heat shrunk around the inner polymeric layer, with the coiled member 32 embedded in one or both layers. Typically, the extruded single or multilayered polymeric tube is necked to reduce the inner and outer diameter thereof. In a presently preferred embodiment, the reduced wall thickness proximal portion of the inner tubular member 20 is then formed by necking the proximal part of the extruded tube to reduce a wall thickness and an outer diameter thereof without reducing an inner diameter thereof. Alternatively, an outer layer of polymeric material may be provided on the outer surface of the inner tubular member distal to the proximal portion of the inner tubular member, as for example by heat shrinking a polymeric tube down onto the distal portion of the inner tubular member, to increase the wall thickness and axial compression stiffness of the inner tubular member distal portion relative to the proximal portion thereof.

The axial compression stiffness and column stiffness of the distal portion of the inner tubular member 20 are about the same as those of the entire length of an inner tubular member in a conventional catheter. However, the bending stiffness of the proximal portion of the inner tubular member 20 is as low as can be practically attained in order to minimize the catheter's overall bending stiffness there.

In one embodiment, the inner tubular member includes one or more portions proximally spaced apart from the bonded portion, along which the outer surface of the inner tubular member proximal portion is bonded to the inner surface of the outer tubular member. In one embodiment, the inner tubular member has a plurality of these portions bonded to the outer tubular member which are intermittently spaced apart from one another with portions of the inner tubular member therebetween which are not bonded to the outer tubular member. FIG. 4B illustrates an embodiment having intermittent proximal bonded portions 30' and 30".

In the embodiment of FIG. 1, the catheter 10 is a rapid exchange catheter. In an alternative embodiment, the catheter is an over-the-wire catheter, so that the guidewire proximal port is at the proximal end of the catheter shaft. FIG. 6 illustrates an over-the-wire type balloon catheter 40 embodying features of the invention, generally comprising a shaft 41 having a proximal shaft section 42 and a distal shaft section 43, and a balloon 44 on the distal shaft section. The elongated shaft comprises an outer tubular member 45 defining an inflation lumen 46, and an inner tubular member 47 defining a guidewire lumen 48 configured to slidably receive a guidewire 23 therein. Inner tubular member 47, extending within the proximal and distal shaft sections 42, 43, extends distally beyond the distal end of the outer tubular member 45 and through the interior of the balloon 44. The guidewire lumen 48 is in fluid communication with a guidewire distal port 49 at the distal end of the shaft 41, and with a guidewire proximal port (not shown) at a proximal end of the shaft 41. An adapter 50 at the proximal end of catheter shaft 41 is configured to provide access to guidewire lumen 48, and to direct inflation fluid into inflation lumen 46 through arm 51. In accordance with the invention, inner tubular member 47 has a stiffness transition and a bonded portion 60, as discussed above in relation to the embodiment of FIG. 1. In the embodiment of FIG. 6, the bonded portion 60 having a length of about 0.1 to about 2 cm, is about 0.07% to about 1.5% of the length of the inner tubular member (the inner tubular member having a length of about 135 to about 145 cm).

Although illustrated as one-piece tubular members, it should be understood that the tubular members forming the catheter shaft 11, 41 may be formed of multiple tubular members or multilayered tubular members. For example, the outer tubular member 19, 45 may comprise multiple tubular members joined end to end, providing increasing flexibility distally along the length of the catheter.

To the extent not previously discussed herein, the various catheter components may be formed and joined by conventional materials and methods. For example, the tubular members forming the catheter shaft 11, 41 can be formed by conventional techniques, such as by extruding and necking materials found useful in intravascular catheters such as polyethylene, polyvinyl chloride, polyesters, polyamide, polyimides, polyurethanes, polyether block amides, and composite materials.

The length of the balloon catheter 10, 40 is generally about 137 to about 145 centimeters, and typically about 143 centimeters for PTCA. The outer tubular member 19, 45 proximal section has an OD of about 0.036 to about 0.043 inch (0.91-1.1 mm), and an inner diameter (ID) of about 0.032 to about 0.036 inch (0.81-0.91 mm), and the outer tubular member 19, 45 distal section has an outer diameter (OD) of about 0.028 to about 0.036 inch (0.70-0.91 mm), and an inner diameter (ID) of about 0.024 to about 0.035 inch (0.60-0.89 mm). The inner tubular member 20, 47 has an OD of about 0.017 to about 0.026 inch (0.43-0.66 mm), and an ID of about 0.015 to about 0.019 inch (0.38-0.48 mm) depending on the diameter of the guidewire to be used with the catheter. The balloon 14, 44 has a length of about 8 mm to about 40 mm, and an inflated working diameter of about 1.5 mm to about 5 mm.

While the present invention has been described herein in terms of certain preferred embodiments, those skilled in the art will recognize that modifications and improvements may be made without departing from the scope of the invention. Moreover, while individual features of one embodiment of the invention may be discussed or shown in the drawings of the one embodiment and not in other embodiments, it should be apparent that individual features of one embodiment may be combined with one or more features of another embodiment or features from a plurality of embodiments.

What is claimed is:

1. A balloon catheter having an elongated shaft with a proximal and a distal end, and a balloon on a distal shaft section, the elongated shaft comprising:

a. an outer tubular member defining at least a section of an inflation lumen in fluid communication with an interior of the balloon, and having a proximal end and a distal end; and b. an inner tubular member defining at least a section of a guidewire lumen, extending in at least a distal section of the outer tubular member and extending in the interior of the balloon, the inner tubular member having a proximal end, a distal end distal to the distal end of the outer tubular member, a length, a bonded portion along which an outer surface of the inner tubular member is bonded to an inner surface of the outer tubular member, a proximal portion proximal to the bonded portion extending from the proximal end of the inner tubular member distally to the bonded portion, and a distal portion distal to the bonded portion extending distally from the bonded portion at least through the balloon interior from a proximal to a distal end of the balloon interior, the proximal portion of the inner tubular member having an axial compression stiffness less than an axial compression stiffness of the distal portion of the inner tubular member, such that a stiffness transition of the proximal portion to the distal portion of the inner tubular member is at the bonded portion.

2. The balloon catheter of claim 1 wherein the bonded portion has a distal end located proximal to the balloon.

3. The balloon catheter of claim 1 wherein the bonded portion has a proximal end located distal to a guidewire proximal port in fluid communication with the guidewire lumen.

4. The balloon catheter of claim 1 wherein the bonded portion has a length of about 0.1 to about 2 mm.

5. The balloon catheter of claim 1 wherein the inner tubular member proximal end is located distal to the proximal end of the shaft in the distal shaft section, and the bonded portion has a length which is about 0.4% to about 8% of the length of the inner tubular member.

6. The balloon catheter of claim 1 wherein the inner tubular member proximal end is located at a proximal end portion of the shaft so that the inner tubular member extends along a proximal shaft section and the distal shaft section, and the bonded portion has a length which is about 0.07% to about 1.5% of the length of the inner tubular member.

7. The balloon catheter of claim 1 wherein the proximal portion of the inner tubular member has a bending stiffness less than a bending stiffness of the distal portion of the inner tubular member.

8. The balloon catheter of claim 1 wherein at least part of the inner tubular member proximal portion has a first wall thickness, and at least part of the inner tubular member distal portion has a second wall thickness which is greater than the first wall thickness.

9. The balloon catheter of claim 8 wherein the part of the inner tubular member having the first wall thickness has an outer diameter smaller than an outer diameter of the part of the inner tubular member having the second wall thickness.

10. The balloon catheter of claim 8 wherein a wall thickness of the inner tubular member along the bonded portion is greater than the wall thickness of the inner tubular member proximal portion.

11. The balloon catheter of claim 1 wherein at least part of the inner tubular member distal portion has a reinforcing member an on outer surface thereof or embedded therein.

12. The balloon catheter of claim 1 wherein at least part of the inner tubular member distal portion is formed of a polymeric tube having at least one layer with fiber reinforcement therein.

13. The balloon catheter of claim 1 wherein the inner tubular member proximal portion comprises a first polymeric material having a first Shore durometer hardness, and the inner tubular member distal portion comprises a second polymeric material having a second Shore durometer hardness which is greater than the first Shore durometer hardness.

14. The balloon catheter of claim 1 wherein the inner tubular member comprises a polymeric tube with a coiled reinforcing member embedded in at least a section thereof.

15. The balloon catheter of claim 14 wherein the coiled reinforcing member extends along an entire length of the inner tubular member.

16. The balloon catheter of claim 14 wherein the coiled reinforcing member extends at least in part within the proximal and distal portions of the inner tubular member.

17. The balloon catheter of claim 14 wherein the coiled reinforcing member in the distal portion of the inner tubular member has a longitudinally extending wire member bonded thereto, or has a coil pitch less than a coil pitch of the part of the coiled reinforcing member in the proximal portion of the inner tubular member.

18. The balloon catheter of claim 1 wherein the bonded portion extends around part of a circumference of the inner tubular member, so that a nonbonded portion of the inner tubular member is radially adjacent to the bonded portion.

19. The balloon catheter of claim 18 wherein the bonded portion extends around about 10% to about 90% of the circumference of the inner tubular member.

20. The balloon catheter of claim 1 wherein the inner tubular member includes one or more proximal bonded portions proximally spaced apart from the bonded portion, along which the outer surface of the inner tubular member proximal portion is bonded to the inner surface of the outer tubular member.

21. The balloon catheter of claim 20 wherein the balloon catheter has two or more of the proximal bonded portions of the inner tubular member bonded to the outer tubular member, which are intermittently spaced apart with portions of the inner tubular member therebetween which are not bonded to the outer tubular member.

* * * * *